United States Patent [19]

Klainer et al.

[11] Patent Number: 5,026,139
[45] Date of Patent: Jun. 25, 1991

[54] FIBER OPTIC REFRACTIVE INDEX SENSOR USING METAL CLADDING

[75] Inventors: Stanley M. Klainer; Dileep K. Dandge; Marcus Butler; Kisholoy Goswami, all of Henderson, Nev.

[73] Assignee: FiberChem Inc., Las Vegas, Nev.

[21] Appl. No.: 501,144

[22] Filed: Mar. 28, 1990

Related U.S. Application Data

[63] Continuation-in-part of Ser. No. 150,197, Jan. 29, 1988, Pat. No. 4,929,049.

[51] Int. Cl.$^5$ .............................................. G02B 6/16
[52] U.S. Cl. .................................. 350/96.29; 356/128; 356/133
[58] Field of Search ................. 350/96.29; 356/128, 356/133

[56] References Cited

U.S. PATENT DOCUMENTS

4,929,049 5/1990 Le Goullon et al. ............ 350/96.29

Primary Examiner—John D. Lee
Assistant Examiner—Stephen W. Barns
Attorney, Agent, or Firm—Henry P. Sartorio

[57] ABSTRACT

A refractive index FOCS has a fiber optic core with a partly light transmissive thin metal film clad of an effective thickness and light transmissivity so that transmission through the core is strongly affected by the refractive index of a surrounding liquid or vapor medium. The metal clad and surrounding medium produce a localized refractive index at the core interface which modulates light transmission through the core as a function of the medium refractive index. The clad is made of platinum, or also of gold, rhodium, palladium, nickel, iron, cobalt, ruthenium, iridium, osmium, zinc, copper, silver, chromium, molybdenum, tungsten, vanadium, niobium, tantalum, titanium, zirconium or hafnium. The clad is also made of oxides of these metals, or metal compounds or alloys. With a fluorescent tip, the changes in the fluorescent signal are a measure of the medium refractive index. With a reflective tip, the changes in the reflected signal are measured. In a linear configuration, source and detector are placed at opposite ends of the fiber and changes in the transmitted signal are measured as a function of refractive index. Multiple measurements with multiple clads of different specificity can be made. The multiple clads can be on a single fiber or on separate fibers.

25 Claims, 4 Drawing Sheets

FIBER OPTIC REFRACTIVE INDEX SENSOR USING METAL CLADDING

RELATED APPLICATIONS

This application is a continuation-in-part (CIP) of application Ser. No. 150,197 filed Jan. 29, 1988, now U.S. Pat. No. 4,929,049 issued May 29, 1990.

BACKGROUND OF THE INVENTION

The invention relates generally to fiber optic sensors, and more particularly to fiber optic sensors for measuring refractive index.

A fiber optic is an optical waveguide which transmits light by total internal reflection (TIR) at the core/clad interface. The critical angle $A_c$ for TIR is determined by the ratio of the refractive index $N_2$ of the clad to the refractive index $N_1$ of the core: $A_c = \sin^{-1}(N_2/N_1)$. Thus the index of the clad must be less than the core for TIR to occur.

Optical fibers have been used in a wide variety of sensors, known as "optrodes" or "fiber optic chemical sensors" (FOCS), which are designed to measure the presence of various chemical species or the value of various parameters such as pressure or temperature. In most cases a signal from a reactant, e.g. a fluorescent signal from a fluorescent dye which interacts with the desired chemical species or is affected by the desired physical parameter, is transmitted through the fiber to a detector. These sensors are generally limited by being specific to a single chemical species or physical parameter; thus each sensor is based on its own unique chemistry. U.S. Pat. No. 4,846,548 issued July 11, 1989 is directed to a more generalized fiber optic sensor methodology in which the principle of detection is based on how the operating characteristics of the fiber itself are modified as the result of the presence of the desired species. The use of this sensor principle allows the fabrication of many different sensors which are sensitive to particular species or even groups of species. However, it would also be desirable to have available a more general sensor which can detect and differentiate a wide variety of species. Since different species usually have different refractive indexes, a single sensor which can measure refractive index would be able to detect the presence of different species. Thus, such a sensor would not be species specific but would be a more universal detector.

SUMMARY OF THE INVENTION

Accordingly, it is an object of the invention to provide a fiber optic sensor which measures refractive index.

It is also an objective of the invention to provide a fiber optic sensor which can identify a wide variety of different species on the basis of different refractive indexes.

The invention is a fiber optic sensor for measuring refractive index which has a fiber optic core with a light porous thin film metal clad which produces a controlled leakage of light as a function of the refractive index of the surrounding medium. The thin film is thus only partly, but not totally, transmissive to light The thin film metal clad is designed to produce a localized refractive index at the core interface when the clad contacts a surrounding medium which modulates the transmission of light through the core as a function of the refractive index of the medium. In one embodiment, the sensor has a fluorescent tip formed of a fluorescent dye immobilized on the tip of the fiber. An excitation signal is transmitted through the fiber to the tip and the fluorescent emission is detected through the fiber. In a second embodiment a (silvered) reflective tip is formed at the end of the fiber so that an incident signal is transmitted back. In a third embodiment, the source and detector are positioned at opposite ends of the fiber so a transmitted signal is detected. The change in refractive index of the medium (liquid or vapor or water emulsion) surrounding the fiber changes the transmission characteristics which results in a signal change at the detector. The thin metal film is of a thickness and is sufficiently light porous or light transmissive such that the leakage of light through the thin film is modulated as a function of the refractive index of the surrounding medium, which may be in liquid or vapor (gas) state. In one embodiment, platinum (Pt) paint is applied on the side of a fiber core and is then heated with a torch to remove the organic base, leaving a thin porous platinum film. Another method of forming the clad is to paint with hydrogen hexachloroplatinate(n)hydrate and torch. In addition to platinum other metals including gold (Au, rhodium (Rh), and palladium (Pd) are suitable for the thin film metal clad. Additional metals for the thin film clad include Ti, Zr, Hf, V, Nb, Ta, Cr, Mo, W, Cu, Ag, Zn, Fe, Ru, Co, Ir, Os and Ni. Alternatively, in place of elemental metal, the clad may be formed of metal oxides or metal compounds or alloys. The metal coatings are deposited by various coating techniques.

Different metal clads have specificity to one or more analytes. The specificity of different clads can be used to make simultaneous measurements which yield a better result by subtracting out the effects of other substances. A single fiber optic core can be clad with a metal clad having plurality of adjacent segments, each segment being made of a different metal. Alternately, multiple fiber optic sensors, each with a different metal clad can be used in combination. The clads are chosen with various specificities so that information about the particular analyte of interest can be calculated from the detected signals from each sensor.

BRIEF DESCRIPTION OF THE DRAWINGS

In the accompanying drawings:

FIGS. 5 A, B, C illustrate the operation of the refractive index FOCS.

DETAILED DESCRIPTION OF THE PREFERRED EMBODIMENTS

The invention is a fiber optic sensor with a light porous or partly light transmissive thin metal clad of suitable thickness on a fiber optic core which varies its transmission properties as a function of the refractive index of the surrounding medium (liquid or vapor or water emulsion), thus providing a measure of refractive index The metal clad is formed on and surrounds a length of the core. In one embodiment, excitation light is transmitted through the fiber to a fluorescent tip and the returning fluorescent signal is detected. In a second embodiment, input light is reflected by a (silvered) reflective tip, and the reflected signal is detected. In a third embodiment, input light from a source at one end of the fiber is transmitted through the fiber and the transmitted signal is measured by a detector at the other end of the fiber.

Figure 1A:
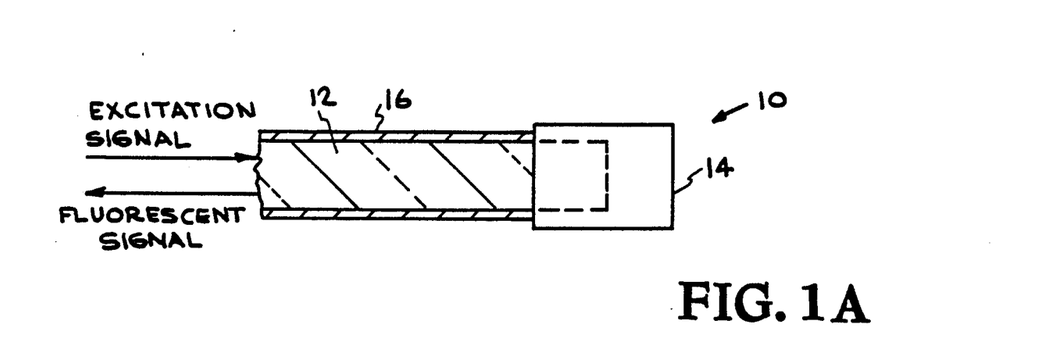
FIGS. 1A, B, C show a fiber optic sensor with thin film metal clad and fluorescent tip, reflective tip, and a linear design, respectively, for measuring refractive index.

As shown in FIG. 1A, sensor 10 has a core 12 with a fluorescent tip 14 and a thin metal clad 16 formed on and surrounding a length of core 12. In a preferred embodiment core 12 is a silica fiber core, e.g an Ensign-Bickford MaxCore HCS fiber, with a core diameter of 400, 600 or 1000 microns, a refractive index of about 1.4, and an attenuation of 10 dB/km at 597 nm. About one inch of the end of a fiber is stripped to the bare core, e.g. by burning off the cladding or removing the cladding chemically. A fluorescent chemical (dye), e.g. Rhodamine B, is attached to the distal end of the fiber core. The fluorescent material may be immobilized or impregnated at the tip in any suitable manner. One method of attaching the fluorophore (fluorescer) is to close a length of shrink tubing onto the fiber core, leaving the distal end open. A grain of Rhodamine B is placed in the open end of the shrink tubing which is then filled with methanol or other solvent to dissolve the dye. A small drop of cyanoacrylate ester (super glue) is then placed on the open end and the tip is heated, e.g. with a hot air gun, to seal the open end to form a fluorescent sack. Optical adhesive, e.g. Norland #61, is then coated on the outside of the entire fluorescent sack surface of the shrink tubing to completely seal the fluorophore.

Figure 1B:
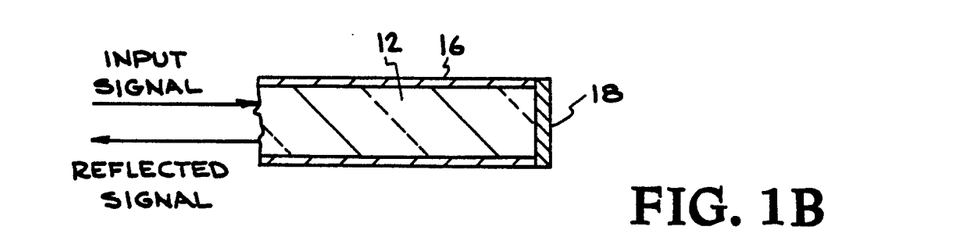

In the embodiment of FIG. 1B a reflective tip 18 is formed onto the end of fiber optic core 12 with its thin film metal clad 16. In the linear (dual end) embodiment of FIG. 1C a portion of fiber optic core 12 is clad with thin metal film 16.

The principle of operation of an optical fiber depends on the refractive index of the material at the core interface. In order for the core to transmit light efficiently, the core must be clad with a material of lower refractive index than the core. With the clad removed, light is transmitted very inefficiently. As the core is placed into various media, the light is transmitted with an efficiency which depends on the refractive index of the medium. The medium, in essence, becomes the clad. The lower the refractive index of the medium, the more light is transmitted through the core. If the medium has a higher refractive index than the core, then no reflection will occur and all the light will be lost.

In accordance with the invention, a thin metal clad of an effective light porosity or transmissivity on the fiber core enhances the change in light transmission of the core as a function of the refractive index of the surrounding medium. The light porosity of the clad is a function of the clad material, its thickness and its physical characteristics such as physical porosity and crystalline structure. The metal clad is of suitable thickness to produce a gradient refractive index at the core-metal clad interface as a result of material from the surrounding medium that is absorbed by the metal clad. The preferred thickness is in the range of greater than about 50 Å up to about 10 microns. A thickness of about one quarter the wavelength of the excitation light may be used. This localized refractive index at the boundary is directly proportional to the amount of material adsorbed/absorbed and also its refractive index, so that the amount of light leaking through the fiber depends on the refractive index of the medium. This substantially modulates a light signal transmitted through the core, producing a detectable measure of refractive index. Thus, the thin metal clad on the core amplifies the effect and provides greater sensitivity, producing a simple, rugged and practical refractive index sensor. In the first embodiment platinum (Pt) paint (Engelhard #A4338 platinum ink) was placed on the side of the bare core. The organic components base of the paint was removed by burning off with a torch to leave a thin shiny Pt coat on the fiber core. Alternatively the core is painted with hydrogen hexachloroplatinate(N)hydrate and torched. Thin films of other materials such as gold (Au), rhodium (Rh) and palladium (Pd) may also be formed. Nickel (Ni) is also of particular interest.

The metal claddings that respond in a similar way to liquids or vapors with different refractive indexes include:

(1) group IVB elements: Titanium (Ti), Zirconium (Zr), Hafnium (Hf)
(2) group VB elements: Vanadium (V), Niobium (Nb), Tantalum (Ta)
(3) group VIB elements: Chromium (Cr), Molybdenum (Mo), Tungsten (W)
(4) group IB elements: Copper (Cu), Silver (Ag). Gold (Au)
(5) group IIB elements: Zinc (Zn), Cadmium (Cd)
(6) group VIII elements: Iron (Fe), Ruthenium (Ru), Cobalt (Co), Rhodium (Rh), Nickel (Ni), Palladium (Pd), Platinum (Pt), Iridium (Ir), Osmium (Os)
(7) Oxides of the above metals
(8) Metal compounds or alloys such as:
  (a) group II-VI compounds: including but not limited to ZnSe, ZnTe, CdS, CdTe, MgTe, ZnS
  (b) group III-V compounds: including but not limited to BN, GaAs, InAs, InSb, AlN, GaN, InN
  (c) group I-VII compounds: including but not limited to CuCl, CuBr, AgI
  (d) sphalerite structure compounds: including but not limited to $Ga_2Te_3$, $ZnSnP_2$, $ZnSnAs_2$
  (e) Wurtzite structure compounds: including but not limited to SiC, MnS, MnSe, MnTe, $Al_2Se_3$
(f) group I, III, VI compounds: including but not limited to $CuGaTe_2$, $CuGaSe_2$, $CuLaS_2$
  (g) group II. IV, V compounds: including but not limited to $ZnGeP_2$, $CdGeP_2$, $ZnGeAs_2$, $ZnSnAs_2$ These metal coatings can be deposited on the fiber optic surface by sputtering, brush coating, vacuum deposition, plasma coating or by any other technique that can form either a homogeneously or heterogeneously coated surface. Either inorganic or organometallic compounds could be employed to deposit metal coating on the fiber. Metals can also be deposited from their elemental states. Final coating deposited on the fiber can be in the form of either elemental metal or any of its oxides, or a metal compound or alloy.

The metal clad, according to the invention, must be of a suitable and effective thickness (neither too thin nor too thick) so that the core does not see a constant index (e.g. either the metal itself or the actual index of the medium). Instead the clad must be of such a thickness that the core sees an index which is related to the index of the medium in the immediate vicinity of the core, and which significantly modulates light transmission through the core for a wide range of values of refractive index of the medium, including values greater than the index of the core.

When the Pt coated core was placed into various solvents, the sensitivity was markedly increased over the core alone. Thus a thin film of Pt or the other metals listed above can be applied to the side of the fiber core by painting, sputtering, or other suitable method such as plating from solution. The layer is heated, if necessary, to remove organic components. A very thin film, e.g., down to a few monolayers or less, in some cases is desired if it is sufficiently partly transmissive to produce the desired controlled light leakage. The thickness of the thin film in combination with other properties of the clad that determine its transmissivity to light is important, an effective thickness allows the transmission of the fiber core to be strongly affected by the refractive index of the surrounding medium. The clad must have an effective light porosity or transmissivity that produces a controlled leakage of light as a function of the refractive index of any surrounding medium. The clad must thus be only partly, or not totally, transmissive to light. The clad must produce a refractive index sensitive modulation of the light transmission through the core. The thickness should be greater than about 50 Å and less than about 10 microns to produce significant variations in the detector signal so the surrounding medium can affect transmission. A typical thickness may be about a quarter wavelength of the input light, which for visible light 4000-7500 Å is a thickness on the order of 1000-2000 Å. Preferably, the clad thickness is in the range of 50 Å to 10 microns.

Figure 1C:
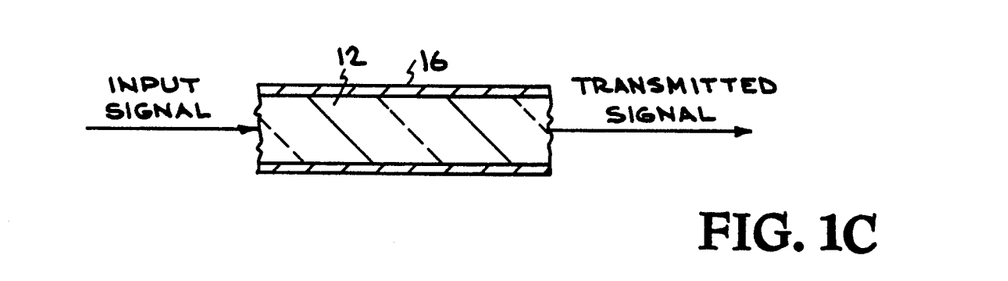
Figure 2:
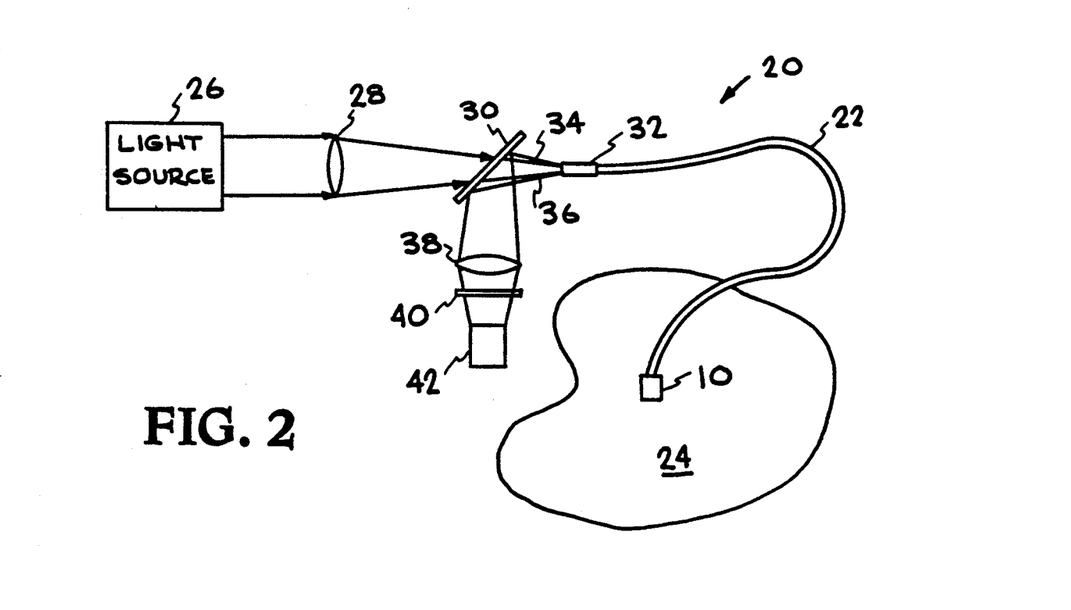
FIG. 2 is sensor system for measuring refractive index of a sample.

A sensor system 20 is illustrated in FIG. 2. A sensor 10, as shown in FIG. 1A. is formed on one end of an optical fiber 22 and placed in a sampling region 24. Light from a light source 26, e.g., an argon laser, or a tungsten halogen lamp or a light emitting diode, is focused by lens 28 through dichroic mirror 30 and into the opposite end 32 of fiber optic 22. This excitation light 34 is transmitted by the fiber to sensor 10 to excite the fluorophore (fluorescer). The returning fluorescent signal 36 is reflected at dichroic mirror 30 and passes through lens 38 and filter 40 into detector 42. The signal received by detector 42 is a measure of the refractive index of the medium in sample region 24. Similar systems can be formed with the sensor of FIG. 1B where the reflected signal is measured instead of a fluorescent signal, or with the sensor of FIG. 1C where the detector is placed at the opposite end of the fiber from the source and the transmitted signal is measured. While visible light may be used, a wider range of wavelengths, from ultraviolet to infrared may also be used to practice the invention.

Figure 3:
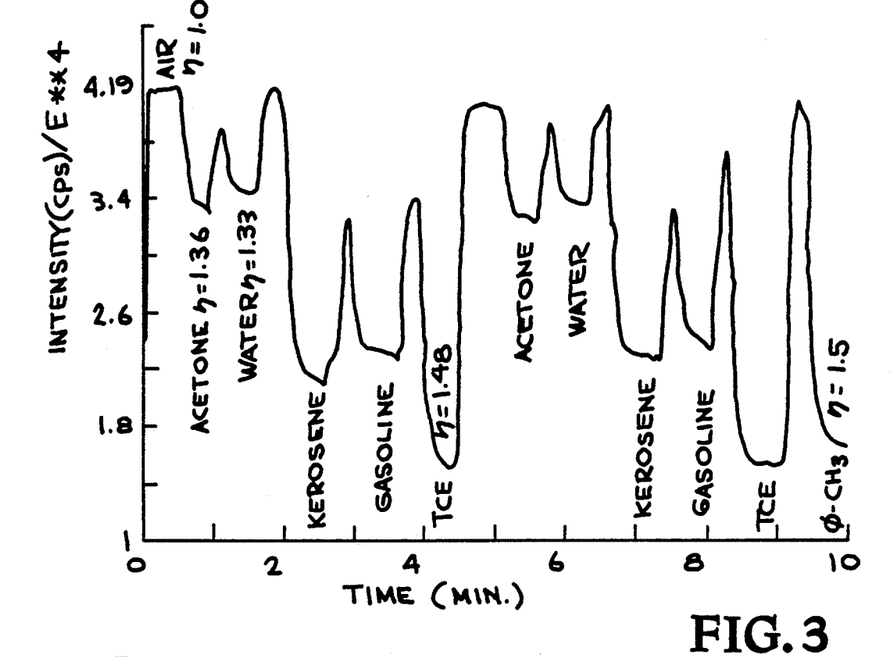
FIG. 3 is a graph of signal intensity as a function of solvent refractive index for a series of different solvents.
Figure 4:
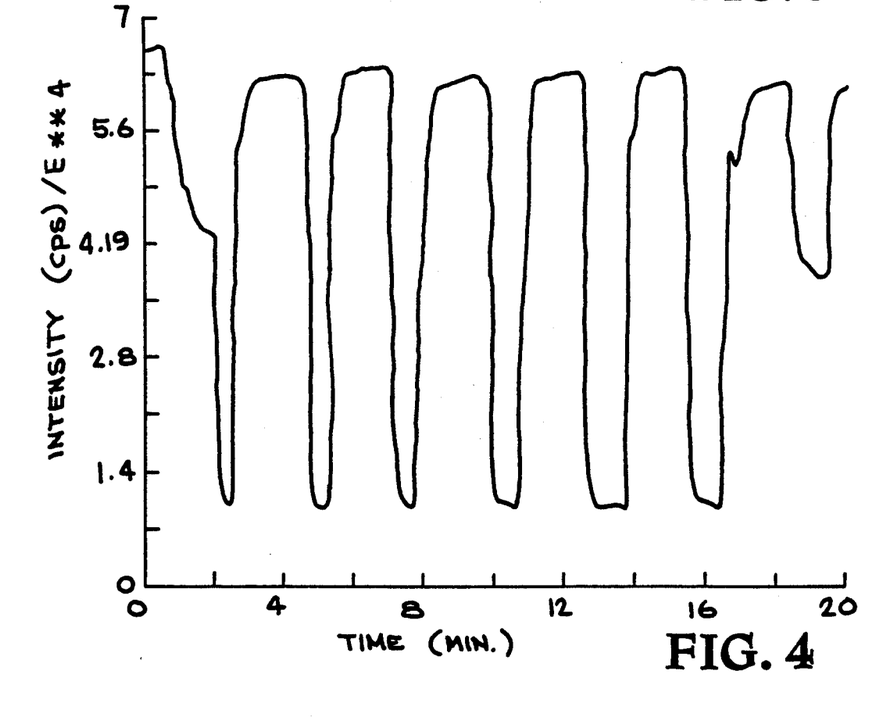
FIG. 4 is a graph of the response of a gasoline sensor to gasoline vapors and liquid.

FIG. 3 illustrates the response of a general refractive-index FOCS according to the invention where a number of different solvents are sequentially flowed over the sensor. The intensity variations at the detector clearly differentiate between different solvents (different refractive indexes). The sensor quickly recovers from one sample solvent to another and the measurements are reproducible, i.e., a similar detector intensity is produced by repeating a solvent. The index of a glass core is about 1.4 and a modulated signal is produced even for a medium with a larger refractive index. This occurs because the metal clad produces a localized index at the core-clad interface which is less than the index of the medium. FIG. 4 shows the response of a refractive index sensor to repetitive samples of gasoline. The intermediate peaks at the beginning and end are gasoline vapor while the rest is liquid.

Figure 5A:
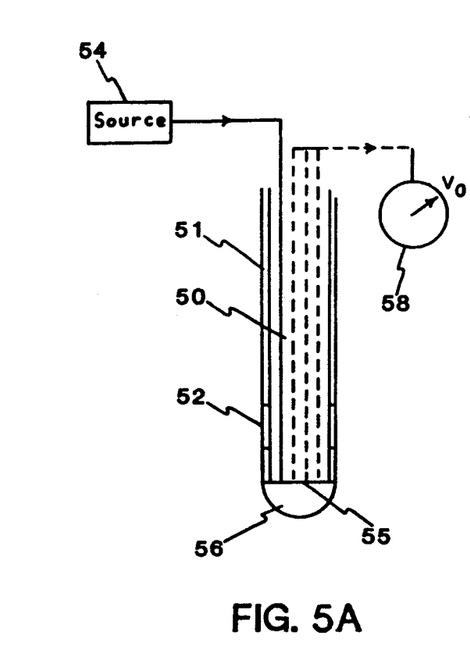
Figure 5B:
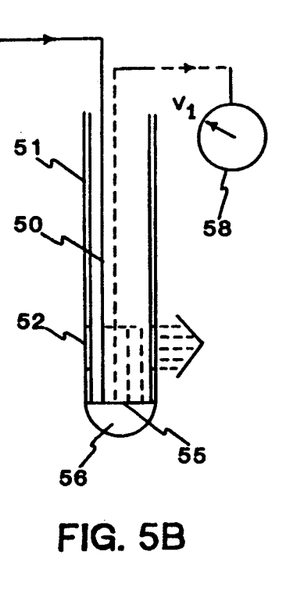
Figure 5C:
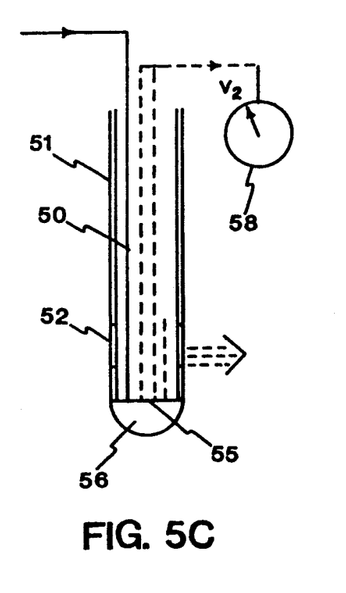

The operation of the refractive index FOCS is illustrated in FIGS. 5A, B and C. A fiber optic core 50 has a thin film metal clad 52 replacing a portion of the regular clad 51. Light from a source 54 is input into the core. Tip 56 at end 55 of the fiber may include a fluorophore or may be reflective (or an alternate linear or dual end fiber optic arrangement may be used). The intensity of the light signal from the fiber optic core 50 is measured by detector 58 and depends on the refractive index of the medium which depends on the concentration of the particular chemical species present.

As shown in FIG. 5A, in the absence of analyte, e.g.. hydrocarbons, the return signal is high (in light intensity) showing higher voltage $V_O$. The index produced at the core interface is produced by the metal clad and air, so it is vary low and results in the maximum light transmission. As the concentration of analyte on the FOCS surface increases, the returning light signal and hence voltage drops and is directly proportional to the concentration of the analyte and to the refractive index of the analyte. FIG. 5B shows the case for 100% sample concentration (highest refractive index of the medium) where light transmission is most reduced (maximum light leakage since the metal clad-medium produce a high localized index) and the detector signal is a minimum $V_1$. FIG. 5C shows the case for an intermediate sample concentration (lower refractive index medium) where an intermediate detector signal $V_2$ is produced (since the localized index and light leakage are intermediate).

In the examples given below in Table I, the initial signal (voltage) is given as $V_O$ and the final signal (volts) is given as V. In qualitative tests, $V_O$ was obtained in empty 4 L glass jars and V was obtained in the presence of analyte vapor which was present as liquid-vapor equilibrium (saturated or near saturated vapor).

In the quantitative measurements described below,
$V_O$ = voltage in the absence of analyte
V = voltage in the presence of a given amount of analyte.

As soon as the FOCS is withdrawn from the analyte atmosphere, the original signal level is attained showing the instant reversibility of the sensor. The following empirical equation describes the performance of the FOCS.

metal coating + analyte = change in refractive index = modulation of light traveling through the fiber optic Table I shows the detector values for a number of different metal clads and for a number of analytes measured with each metal clad. Accordingly a particular metal clad can be designed to detect a particular analyte, although each analyte can be detected by a number of different metal clads. Certain metals are particularly sensitive to certain analytes.

TABLE I

|  | $V_0$ | V |
|---|---|---|
| Ru |  |  |
| Gasoline | 7.27 | 3.87 |
| Benzene | 7.00 | 4.19 |

TABLE I-continued

|  | $V_0$ | V |
|---|---|---|
| Xylene | 7.38 | 4.39 |
| Toluene | 7.07 | 4.10 |
| V |  |  |
| Gasoline | 6.85 | 5.80 |
| Benzene | 5.32 | 3.79 |
| Zr |  |  |
| Gasoline | 8.20 | 5.89 |
| Benzene | 8.00 | 2.28 |
| Xylene | 7.68 | 3.62 |
| Toluene | 7.51 | 4.57 |
| Ni |  |  |
| Gasoline | 9.46 | 6.74 |
| Benzene | 7.48 | 1.07 |
| Xylene | 8.56 | 1.27 |
| Toluene | 8.16 | 1.77 |
| Pd |  |  |
| Gasoline | 7.51 | 4.92 |
| Benzene | 8.00 | 6.78 |
| Xylene | 7.44 | 5.00 |
| Fe |  |  |
| Benzene | 8.96 | 1.65 |

Table II lists a number of illustrative metal surfaces and various gases which have been found to be adsorbed on the metal surface. The adsorbability of the gases may depend on the crystal form and/or orientation of the metal layer. However, in the process of forming the metal clad on the fiber optic core, particular crystal forms of the metal can be reproducibly obtained by controlling the process parameters, e.g. temperature and pressure, so that a sensor tailored to a specific gas can be obtained. Thus, a sensor with a metal clad of preselected crystal structure can be produced for use with a desired analyte. Table III similarly lists a number of illustrative metal surfaces and various organic compounds (hydrocarbons) which have been found to be absorbed on the metal surface. Certain metals, and in some cases certain crystal forms of some metals, are thus particularly suitable for the metal clad for detection of certain hydrocarbons. The lists in Tables II and III are only for purposes of illustration and are not exhaustive of all possible combinations. Further information about adsorption of gases by metal surfaces is contained in *Chemistry In Two-Dimensional Surfaces*, Gabor A. Somorjai Cornell Univ. Press, Ithaca, N. Y., 1981 particularly Tables 5.2-5.7, pp. 210-241 which are herein incorporated by reference.

The specificity of different metal clads to various analytes allows more specific analysis of an analyte mixed with other substances. The invention further includes multiple measurement methods and apparatus. Since more than one clad may be available for a particular analyte, but each clad will not have the same absorption coefficients to other analytes, a more complex measurement method and sensor structure can be used to determine the presence of a selected analyte out of a mixture of several different analytes. To detect analyte A in a mixture of analytes A and B, it would be most desirable to find a single metal surface that is specific to A. However if one cannot be found, two sensors can be used, one which has a clad which responds to both A and B and one of which has a clad which responds to B but not A. By subtracting the measurement obtained from the second sensor from that of the first sensor, a measure of analyte A is obtained. Alternatively, if a specific metal clad is not available for either A or B, then clads are chosen which have different absorption coefficients for A and B, and the concentration of A and B are obtained by solving an algorithm for two unknowns. The dual sensor approach can be extended to multiple sensors for more than two analytes and can be implemented in a variety of ways, using either a single fiber optic or multiple fiber optics.

Figure 6A:
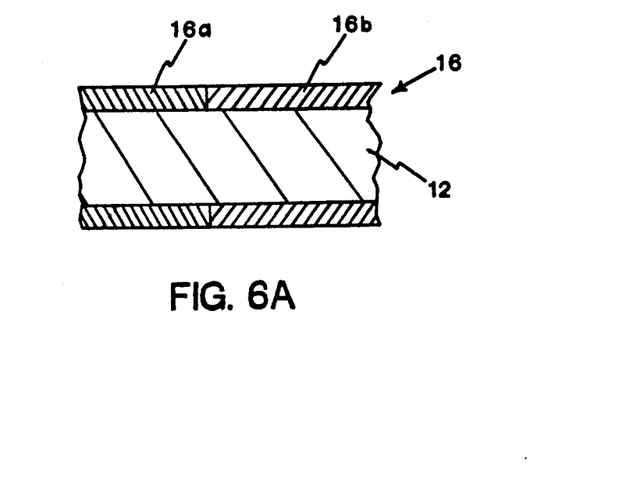
FIG. 6A shows a fiber optic core with metal clad which is made of adjacent segments of different metals.
Figure 6B:
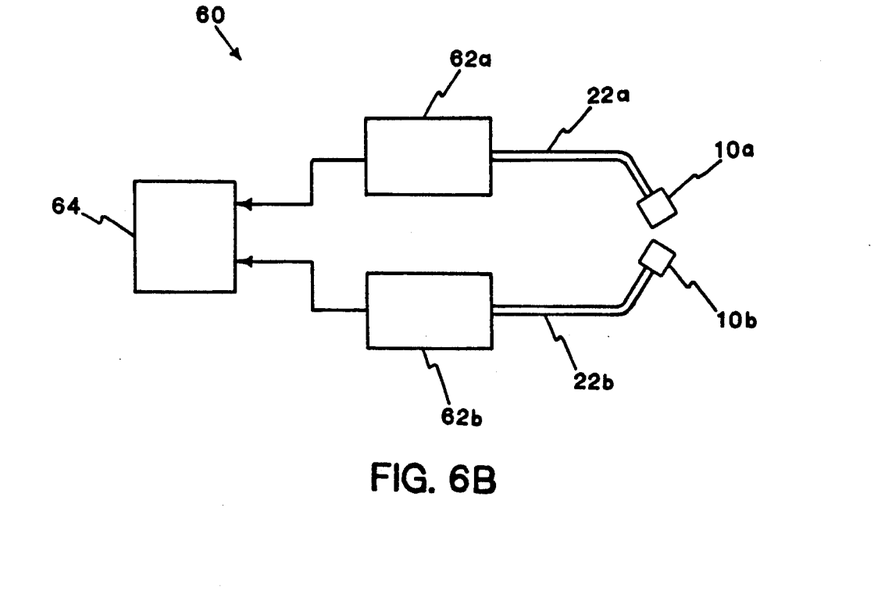
FIG. 6B is a schematic view of a multiple sensor system.

One embodiment of the dual/multiple measurement approach is to form the metal clad 16 of FIGS. 1A-C of an alloy or two (or more) metals which are specific to the analytes of interest. In a second embodiment, as shown in FIG. 6A, metal clad 16 on core 12 is made up of a plurality of adjacent segments 16a, 16b, etc. each of which is a different metal with preferential absorption coefficients to one or more of the analytes of interest. In a third embodiment, illustrated in FIG. 6C, a detection system 60 has a first fiber optic 22a with a first metal clad sensor 10a and a second fiber optic 22b with a second metal clad sensor 10b, each of which is connected to a respective source/detector 62a, 62b. There is no limit to the number of fibers which can be used to perform the requisite analysis of a sample. Source/detector units 62a, 62b could be combined into a single unit or share some components, e.g., a common source or other parts of the optical train. The function of source/detector units 62a, 62b is to provide a source signal to each sensor 10a, 10b and to produce a detector signal from each sensor 10a, 10b. Each sensor 10a, 10b is of any of the types shown in FIGS. 1A-C and has a different metal clad from the other. Each metal clad is preselected for its affinity to particular analytes. The combination is chosen to improve the specificity to the analyte of interest. The detector signals from source/detector units 62a, 62b are input into a processing unit 64 which performs the necessary data analysis to yield information about the analyte(s) of interest. Inasmuch as metal absorbers are not perfect, e.g., those showing "0" absorption may absorb slightly and those showing complete absorption may not collect everything, the processor contains an algorithm which properly weights the sensor response according to the absorption coefficient of the metal for the targe species. Although the illustrative embodiment of FIG. 6B has been shown with two sensors, the method and apparatus can, of course, be extended to more than two sensors each with a different metal clad, including different crystal forms of the same metals.

TABLE II

| SURFACE | ADSORBED GAS |
|---|---|
| Al(111), (100), (110) | $O_2$ |
| Au(111) | $O_2$ |
| (100) | $H_2S$, CO, Xe |
| Cu(111) | $O_2$, CO, $Cl_2$, $H_2S$, Xe |
| (100) | $O_2$, CO, $N_2$ |
| (110) | $O_2$, CO, $H_2O$, $H_2S$, Xe |
| Cu/Ni(111) | CO |
| (110) | $O_2$, CO, $H_2S$ |
| Fe(111) | $O_2$, $NH_3$, $H_2$ |
| (100) | $O_2$, CO, $H_2S$, $H_2$, $NH_3$, $H_2O$ |
| (110) | $O_2$, CO, $N_2$, $H_2$, $H_2S$ |
| Fe/Cr(100), (110) | $O_2$ |
| Mo(111) | $O_2$, $H_2S$ |
| (100) | $O_2$, CO, $H_2$, $N_2$, $H_2S$ |
| (110) | $O_2$, CO, $CO_2$, $H_2$, $N_2$, $H_2S$ |
| Ni(111) | $O_2$, CO, $CO_2$, $H_2$, NO, $H_2S$, $H_2Se$, $Cl_2$ |
| (100) | $O_2$, CO, $CO_2$, $H_2$, $H_2S$, Te, Xe |
| (110) | $O_2$, CO, $H_2$, NO, $H_2O$, $H_2S$, $H_2Se$ |
| NiO(101) | $H_2$, $H_2S$, $Cl_2$ |
| Pt(111) | $O_2$, CO, $H_2$, NO, $H_2O$, $S_2$, N |
| (100) | $O_2$, CO, $H_2$, NO, N, $H_2S$, $S_2$ |
| (110) | $O_2$, CO, $C_3O_2$, NO, $H_2S$ |
| Rh(111), (100) | $O_2$, CO, $CO_2$, $H_2$, NO |
| (110) | $O_2$, CO |

TABLE II-continued

| SURFACE | ADSORBED GAS |
|---|---|
| Zn(0001) | $O_2$ |
| ZnO(1010) | $O_2$ |

TABLE III

| SURFACE | ADSORBED GAS |
|---|---|
| Fe(100) | $C_2H_4$ |
| Ir(111) | $C_2H_2$, $C_2H_4$, cyclohexane, benzene |
| (100) | $C_2H_2$, $C_2H_4$, benzene |
| (110) | $C_2H_4$, benzene |
| Mo(100) | $CH_4$ |
| Ni(111) | $CH_4$, $C_2H_2$, $C_2H_4$, $C_2H_6$, cyclohexane, benzene |
| (100) | $CH_4$, $C_2H_2$, $C_2H_4$, $C_2H_6$, benzene |
| (110) | $CH_4$, $C_2H_4$, $C_2H_6$, $C_5H_{12}$ |
| Pt(111) | $C_2H_2$, $C_2H_4$, n-butane, n-pentane, n-hexane, n-heptane, n-octane, cyclohexane, benzene, toluene, naphthalene, pyridine, m-xylene, mesitylene, T-butylbenzene, N-butyl-benzene, aniline, nitrobenzene, cyano-benzene |
| (100) | $C_2H_2$, $C_2H_4$, benzene naphthalene, pyridine, toluene, M-xylene, mesitylene, T-butylbenzene, N-butylbenzene, aniline, nitrobenzene, cyanobenzene, $C_2N_2$ |
| (110) | HCN, $C_2N_2$ |
| Rh(111), (100), (331) | $C_2H_2$, $C_2H_4$ |

As an example of the multi-sensor approach, form Table II, Mo(111) is reactive to $O_2$ and $H_2S$ while Al(111) is sensitive to $O_2$ but not to $H_2S$. Therefore, the measurement obtained with the Al clad sensor can be substracted from the measurement with the Mo clad sensor to provide a more accurate measure of $H_2S$. As another example, Cu and Ni both respond to numerous gases, including CO, so Cu and Ni sensors could be used in combination. However Cu/Ni(111) appears to be specific to CO, demonstrating the ability to use an alloy for a specific measurement, but Cu/Ni(110) is not as specific to CO so is not as good, showing the preference of certain crystal forms or orientations. As a third example, to measure $C_2H_6$, use Ni(111) which responds to $CH_4$, $C_2H_2$, $C_2H_4$ and $C_2H_6$, subtract measurements from Mo(100) for $CH_4$, Fe(100) for $C_2H_4$, Ir(100) for $C_2H_2$ and $C_2H_4$ and benzene, Ir(110) for $C_2H_4$ and benzene. Changes and modifications in the specifically described embodiments can be carried out without departing from the scope of the invention which is intended to be limited only by the scope of the appended claims.

We claim:

1. A fiber optic sensor for measuring refractive index of a surrounding medium, comprising:
   a fiber optic core;
   a thin film metal clad of metal or metal oxide or other metal compound or alloy formed on and surrounding the fiber optic core, the metal clad having an effective thickness and light transmissivity which in combination with the surrounding medium produces a localized refractive index and a controlled leakage of light which modulates the transmission of light through the fiber optic core as a function of the refractive index of the surrounding medium.

2. The sensor of claim 1 wherein the metal clad has a thickness of greater than about 50 Å and less than about 10 microns.

3. The sensor of claim 1 further comprising:
   a light source operatively associated with the fiber optic core for inputting a light signal into the core;
   detection means operatively associated with the fiber optic core for detecting a light signal from the fiber optic core.

4. The sensor of claim 3 wherein the light source is operatively associated with one end of the fiber optic core and the detection means is operatively associated with the other end of the fiber optic core.

5. The sensor of claim 1 wherein the metal clad is selected from:
   (a) group IB elements: Copper (Cu), Silver (Ag), Gold (Au);
   (b) group IIB elements: Zinc (Zn), Cadmium (Cd);
   (c) group IVB elements: Titanium (Ti), Zirconium (Zr), Hafnium (Hf).,
   (d) group VB elements: Vanadium (V), Niobium (Nb), Tantalum (Ta);
   (e) group VIB elements: Chromium (Cr), Molybdenum (Mo), Tungsten (W)
   (f) group VIII elements: Iron (Fe), Ruthenium (Ru), Cobalt (Co, Rhodium (Rh), Nickel (Ni), Palladium (Pd), Platinum (Pt), Iridium (Ir), Osmium (Os);
   (g) oxides of the above metals;
   (h) group II–VI compounds: ZnSe, ZnTe, CdS, CdTe, MgTe, ZnS;
   (i) group III–V compounds: BN, GaAs, InAs, InSb, AlN, GaN, InN;
   (j) group I–VII compounds: CuCl, CuBr, AgI;
   (k) sphalerite structure compounds: $Ga_2Te_3$, $ZnSnP_2$, $ZnSnAs_2$;
   (l) Wurtzite structure compounds: Mns, MnSe, SiC, MnTe, $Al_2Se_3$;
   (m) group I, III, VI compounds, $CuGaTe_w$, $CuGaSe_w$, $CuLaS_2$;
   (n) group II, IV, V compounds: $ZnGeP_2$, $CdGeP_2$, $ZnGeAs_2$, $ZnSnAs_2$.

6. The sensor of claim 4 wherein the metal clad has a thickness of greater than about 50 Å and less than about 10 microns.

7. The sensor of claim 5 further comprising;
   a light source operatively associated with the fiber optic core for inputting a light signal into the core;
   detection means operatively associated with the fiber optic core for detecting a light signal from the fiber optic core.

8. The sensor of claim 5 further comprising a fluorescent material immobilized at a tip of the fiber optic core with the thin film metal clad adjacent to the fluorescent tip.

9. The sensor of claim 1 further comprising a fluorescent material immobilized at a tip of the fiber optic core with the thin film metal clad adjacent to the fluorescent tip.

10. The sensor of claim 1 further comprising a reflective tip formed at a tip of the fiber optic core with the thin film metal clad adjacent to the reflective tip.

11. The sensor of claim 1 wherein the thin film metal clad comprises a plurality of adjacent segments of different materials, each segment having a different specificity to components of the surrounding medium.

12. The sensor of claim 11 further comprising:
   a light source operatively associated with the fiber optic core for inputting a light signal into the core;
   detection means operatively associated with the fiber optic core to detect
   signals produced by modulation by each segment of the core;

processing means for calculating information about a particular component of interest from the signals produced by modulation by the metal clad segments.

13. A method of detecting the refractive index of a medium, comprising:

providing a fiber optic sensor comprising a fiber optic core and a thin film metal clad of metal or metal oxide or other metal compound or alloy formed on and surrounding the fiber optic core, the metal clad having an effective thickness and light transmissivity which in combination with a surrounding medium produces a localized refractive index and a controlled leakage of light which modulates the transmission of light through the fiber optic core as a function of the refractive index of the surrounding medium;

contacting the thin film metal clad with the medium;
inputting a light signal into the core;
detecting changes in intensity of a light signal transmitted from the core.

14. The method of claim 13 wherein the metal clad is selected from;
 (a) group IB elements: Copper (Cu), Silver (Ag), Gold (Au);
 (b) group IIB elements: Zinc (Zn), Cadmium (Cd);
 (c) group IVB elements: Titanium (Ti), Zirconium (Zr), Hafnium (Hf);
 (d) group VB elements: Vanadium (V), Niobium (Nb), Tantalum (Ta);
 (e) group VIB elements: Chromium (Cr), Molybdenum (Mo), Tungsten (W);
 (f) group VIII elements: Iron (Fe), Ruthenium (Ru), Cobalt (Co). Rhodium (Rh), Nickel (Ni), Palladium (Pd), Platinum (Pt), Iridium (Ir), Osmium (Os);
 (g) oxides of the above metals;
 (h) group II-VI compounds: ZnSe, ZnTe, CdS, CdTe, MgTe, ZnS;
 (i) group III-V compounds: BN, GaAs, InAs, InSb, AlN, GaN, InN;
 (j) group I-VII compounds: CuGl, CuBr, AgI;
 (k) sphalerite structure compounds: $Ga_2Te_3$, $ZnSnP_2$, $ZnSnAs_2$;
 (l) Wurtzite structure compounds: MnS, MnSe, SiC, MnTe, $Al_2Se_3$;
 (m) group I, III, VI compounds: $CuGaTe_2$, $CuGaSe_2$, $CuLaS_2$;
 (n) group II, IV, V compounds: $ZnGeP_2$, $CdGeP_2$, $ZnGeAs_2$, $ZnSnAs_2$.

15. The method of claim 13 wherein the metal clad is formed of a thickness of greater than about 50 Å and less than about 10 microns.

16. The method of claim 13 wherein the step of providing a sensor is performed by providing a sensor further comprising a fluorescent tip on the fiber optic core, the step of inputting a light signal is performed by inputting a light signal of a wavelength selected to excite fluorescence of the tip and the step of detecting is performed by detecting changes in intensity of a fluorescent signal from the core.

17. The method of claim 13 wherein the step of providing a sensor is performed by providing a sensor further comprising a reflective tip on the fiber optic core and the step of detecting is performed by detecting the intensity of a light signal reflected from the reflective tip back through the fiber optic core.

18. The method of claim 13 further comprising inputting the light signal at one end of the fiber optic core and detecting a transmitted signal at the other end of the fiber optic core.

19. A method of forming a refractive index fiber optic chemical sensor comprising:

providing a fiber optic core;
forming a thin film metal clad of metal or metal oxide or other metal compound or alloy on and surrounding the fiber optic core, the metal clad having an effective thickness and light transmissivity which in combination with a surrounding medium produces a localized refractive index and a controlled leakage of light which modulates the transmission of light through the fiber optic core as a function of the refractive index of the surrounding medium.

20. The method of claim 19 further comprising forming the metal clad of a metal selected from:
 (a) group IB elements: Copper (Cu), Silver (Ag), Gold (Au);
 (b) group IIB elements: Zinc (Zn), Cadmium (Cd);
 (c) group IVB elements: Titanium (Ti), Zirconium (Zr), Hafnium (Hf);
 (d) group VB elements: Vanadium (V), Niobium (Nb), Tantalum (Ta);
 (e) group VIB elements: Chromium (Cr), Molybdenum (Mo). Tungsten (W);
 (f) group VIII elements: Iron (Fe), Ruthenium (Ru), Cobalt (Co), Rhodium (Rh), Nickel (Ni), Palladium (Pd), Platinum (Pt), Iridium (Ir), Osmium (Os);
 (g) oxides of the above metals;
 (h) group II-VI compounds: ZnSe, ZnTe, CdS, CdTe, MgTe, ZnS;
 (i) group III-V compounds: BN, GaAs, InAs, InSb, AlN, GaN, InN;
 (j) group I-VII compounds: CuCl, CuBr, AgI;
 (k) sphalerite structure compounds: $Ga_2Te_3$, $ZnSnP_2$, $ZnSnAs_2$;
 (l) Wurtzite structure compounds MnS, MnSe, SiC, MnTe, $Al_2Se_3$;
 (m) group I, III, VI compounds: $CuGaTe_2$, $CuGaSe_2$, $CuLaS_2$;
 (n) group II, IV, V compounds: $ZnGeP_2$, $CdGeP_2$, $ZnGeAs_2$, $ZnSnAs_2$.

21. The method of claim 19 further comprising forming the metal clad of a thickness of greater than about 50 Å and less than about 10 microns.

22. The method of claim 19 wherein the step of forming a metal clad on the core is performed by sputtering, vacuum deposition, plasma coating, brush coating, or spin coating of said metal.

23. Apparatus for detecting the presence of a particular chemical species, comprising:

a plurality of fiber optic sensors, each sensor having a thin film metal clad on a fiber optic core, each metal clad being of a different material of selected sensitivity to various chemical species;
a light source operatively associated with the plurality of sensors to input a light signal into each sensor;
detection means operatively associated with the sensors to detect signals produced by each metal clad;
processing means for calculating information about one or more species from the detected signals produced by each metal clad.

24. The apparatus of claim 23 wherein each sensor is formed on a separate fiber optic.

25. The apparatus of claim 23 wherein the plurality of sensors are all formed on a single fiber optic with the metal clads forming adjacent segments on the fiber optic core.

* * * * *